(12) United States Patent
Leren et al.

(10) Patent No.: US 11,213,477 B2
(45) Date of Patent: Jan. 4, 2022

(54) COSMETIC COMPOSITION COMPRISING A CHAGA EXTRACT AND USE THEREOF

(71) Applicant: Aqua Bio Technology ASA, Fornebu (NO)

(72) Inventors: Hans Kristian Leren, Oslo (NO); Geir Håvard Kvalheim, Oslo (NO)

(73) Assignee: AQUA BIO TECHNOLOGY ASA, Fornebu (NO)

( * ) Notice: Subject to any disclaimer, the term of this patent is extended or adjusted under 35 U.S.C. 154(b) by 146 days.

(21) Appl. No.: 16/471,790

(22) PCT Filed: Dec. 21, 2017

(86) PCT No.: PCT/EP2017/084134
§ 371 (c)(1),
(2) Date: Jun. 20, 2019

(87) PCT Pub. No.: WO2018/115303
PCT Pub. Date: Jun. 28, 2018

(65) Prior Publication Data
US 2020/0113814 A1 Apr. 16, 2020

(30) Foreign Application Priority Data

Dec. 21, 2016 (GB) ...................... 1621818

(51) Int. Cl.
| | | |
|---|---|---|
| *A61K 36/00* | (2006.01) | |
| *A61K 8/9728* | (2017.01) | |
| *A61K 8/02* | (2006.01) | |
| *A61K 8/66* | (2006.01) | |
| *A61K 8/67* | (2006.01) | |
| *A61Q 19/08* | (2006.01) | |

(52) U.S. Cl.
CPC ............ *A61K 8/9728* (2017.08); *A61K 8/022* (2013.01); *A61K 8/66* (2013.01); *A61K 8/673* (2013.01); *A61K 8/676* (2013.01); *A61K 8/678* (2013.01); *A61Q 19/08* (2013.01); *A61K 2800/30* (2013.01); *A61K 2800/59* (2013.01)

(58) Field of Classification Search
None
See application file for complete search history.

(56) References Cited

U.S. PATENT DOCUMENTS

| | | | |
|---|---|---|---|
| 4,268,499 A | 5/1981 | Keil | |
| 2003/0167556 A1* | 9/2003 | Kelley | .......... A61K 8/35 2/206 |
| 2008/0038300 A1 | 2/2008 | Jaspers et al. | |
| 2009/0043236 A1 | 2/2009 | Kawamura et al. | |

FOREIGN PATENT DOCUMENTS

| | | | |
|---|---|---|---|
| KR | 10-2004-0102558 A | 12/2004 | |
| KR | 10-2004-0102773 A | 12/2004 | |
| KR | 2004102773 A | * 12/2004 | |
| KR | 10-2005-0034833 A | 4/2005 | |
| KR | 10-2005-0038112 A | 4/2005 | |
| KR | 10-0863890 B1 | 10/2008 | |
| KR | 10-2015-0097072 A | 8/2015 | |
| KR | 10-2015-0113513 A | 10/2015 | |
| KR | 10-2016-0123158 A | 10/2016 | |
| KR | 101662185 B1 | * 10/2016 | |
| WO | WO-2005/067499 A2 | 7/2005 | |
| WO | WO-2009/085302 A2 | 9/2009 | |

OTHER PUBLICATIONS

Wolfe et al., "Cellular Antioxidant Activity (CAA) Assay for Assessing Antioxidants, Foods, and Dietary Supplements," J Agric Food Chem. 55(22):8896-907 (2007).
Faass et al., "The Healing Powers of Wild Chaga: An Interview with Cass Ingram, MD," Journal of Health and Healing. 35(4): 6-11 (Dec. 2011) (7 pages).
Hu et al., "Comparative study of antioxidant activity and antiproliferative effect of hot water and ethanol extracts from the mushroom *Inonotus obliquus*," J Biosci Bioeng. 107(1): 42-48 (2009).
Kang et al., "Ergosterol peroxide from Chaga mushroom (*Inonotus obliquus*) exhibits anti-cancer activity by down-reguiation of the beta-catenin pathway in colorectal cancer," J Ethnopharmacol. 173:303-12 (2015) (10 pages).
Ning et al., "Inhibitory effects of a polysaccharide extract from the Chaga medicinal mushroom *Inonotus obliquus* (higher Basidiomycetes), on the proliferation of human neurogliocytoma cells," Int J Med Mushrooms. 16(1): 29-36 (2014) (8 pages).
Oy, "Technical specification sheet: Feno-Chaga™ 50: Spray dried chaga extract powder," (2016) (2 pages).
Oy, "Technical specification sheet: Feno-Chaga™ 25: Microencapsulated chaga extract powder," (2016) (2 pages).
Oy, "Technical specification sheet: Feno-Chaga™ 50L: Liquid chaga extract," (2016) (2 pages).
Youn et al., "Potential anticancer properties of the water extract of Inontus obliquus by induction of apoptosis in melanoma B16-F10 cells," J Ethnopharmacol. 121(12): 221-228 (2009).
Yun et al., "Inonotus obliquus protects against oxidative stress-induced apoptosis and premature senescence," Mol Cells. 31(5): 423-429 (2011) (7 pages).
Zhao et al., "Triterpenoids from Inonotus obliquus and their antitumor activities," Fitoterapia. 101:34-40 (2015) (7 pages).
International Search Report and Written Opinion for International Application No. PCT/EP2017/084134 dated Sep. 2, 2018 (10 pages).
Search Report for British Patent Application No. GB1621818.2, dated Oct 24, 2017 (6 pages).

* cited by examiner

*Primary Examiner* — Qiuwen Mi
(74) *Attorney, Agent, or Firm* — Clark & Elbing LLP (57) ABSTRACT

The present invention relates to a cosmetic composition comprising an extract from *Inonotus obliquus* (Chaga) and in particular to a cosmetic composition comprising: (i) a chaga extract at a concentration of at least about 2.5 mg/ml; and (ii) one or more physiologically or pharmaceutically acceptable excipients and/or diluents, wherein the chaga extract comprises at least about 1% (w/w) of β-glucans and/or at least about 0.10% (w/w) of polyphenolics.

26 Claims, 4 Drawing Sheets

COSMETIC COMPOSITION COMPRISING A CHAGA EXTRACT AND USE THEREOF

The present invention relates to a cosmetic composition comprising an extract from *Inonotus obliquus* (Chaga) and its use in various applications to the skin. In particular, the extract as defined herein, and compositions comprising said extract, is/are useful for altering, preferably improving, the cosmetic appearance of skin and/or improving the vitality or condition and performance of skin.

The skin is one of the more vulnerable organs of the body. Skin is in constant interaction with external stimuli, directly or indirectly, and is frequently exposed to, and affected by, environmental agents. In fact, the skin can be seen as the first point of contact with the outside world. This constant exposure can result in unpleasant and/or unwanted physical and visible changes to the skin, particularly to the cosmetic appearance of skin. Whilst such changes may not threaten the health of an individual, such changes may be physically uncomfortable or visibly disagreeable. Indeed, because the skin is so visible, changes to the appearance of skin can lead to psychological stress. There is therefore a continuing need and demand for effective treatments to maintain, restore or improve the condition (vitality) and performance of the skin, and in particular to restore the youthful appearance of skin.

Skin forms the largest organ of the body, accounting for about 12-16 percent of a person's weight. It performs many vital roles as both a barrier and a regulating influence between the outside world and the controlled environment within our bodies.

Skin consists of 3 layers, namely the epidermis, dermis and subcutis. The epidermis is the uppermost, epithelial layer of the skin. It acts as a physical barrier, preventing loss of water from the body, and preventing entry of substances and organisms into the body. Its thickness varies according to body site.

The epidermis consists of stratified squamous epithelium, i.e. it consists of layers of flattened cells. Skin, hair and nails are keratinised, meaning they have a dead, hardened hydrophobic surface made of a protein called keratin. Epidermis is made impermeable due to its contents of extracellular lipids associated with keratinocytes, especially in the middle layer of the epidermis (*Stratum lucidum*). Mucous membranes (e.g. of the oesophagus, oral pharyngeal cavity, reproductive organs, and others) are mainly non-keratinised and moist. The epidermis has three main types of cell, namely keratinocytes (skin cells), melanocytes (pigment-producing cells) and Langerhans cells (immune cells). The Merkel cell is a fourth, less prevalent, epidermal cell.

The keratinocytes mature and differentiate with accumulation of keratin as they move outwards. They eventually fall or rub off. They form four or five distinct strata, which from the most superficial to the deepest are (i) the *Stratum corneum* (horny layer) with dead, dried-out hard cells without nuclei, (ii) the *Stratum granulosum* (granular layer) with cells containing basophilic granules and outwardly separated from *Stratum corneum* by the thin *Stratum lucidum*, (iii) the *Stratum spinulosum* (spinous, spiny or prickle cell layer) in which the cells become increasingly flattened as they move upward and (iv) the *Stratum basale* (basal layer) with columnar (tall) regenerative cells.

Immediately below the epidermis is the basement membrane, a specialised structure that lies between the epidermis and dermis.

The dermis is the fibrous connective tissue or supportive layer of the skin. The major fibres are collagen fibres and elastin which are interwoven.

The subcutis is the fat layer immediately below the dermis and epidermis. It is also called subcutaneous tissue, hypodermis or panniculus. The subcutis mainly consists of fat cells (adipocytes), nerves and blood vessels.

New epithelial skin cells are created in the skin's lower layer, the *Stratum granulosum*. Over time, cells migrate to the surface of the skin and become more acidic. During their 30 day journey, they die and become saturated with keratin. Keratin and associated lipids are important because they protect the skin from outside elements.

Many factors may contribute to the deterioration in the cosmetic appearance of skin including disease, injury, environmental factors, age, hormone levels, medication, externally applied or ingested materials, genetic conditions or a combination of these and other factors. Age related deterioration in the cosmetic appearance of skin is a universal factor (i.e. chronological ageing). In some instances, deterioration in the cosmetic appearance of skin may be accelerated or accentuated by external factors, such as UV, i.e. photoageing (also known as dermatoheliosis). This deterioration can be seen in irregularities or abnormalities in the skin, which may appear as, e.g. dry skin, wrinkles, fine lines, increased laxity (sagging) or altered pigmentation.

Photoageing is a term used for the characteristic changes induced by chronic UVA and UVB exposure. The deterioration of biological functions and ability to manage metabolic stress is one of the major consequences of the ageing process. Ageing is a complex, progressive process which also leads to functional and aesthetic changes in the skin.

Photoageing is a process of ageing of the skin attributed to continuous, long-term (chronic) exposure of skin to ultraviolet (UV) radiation of approximately 245-290 nm, which may be from natural or synthetic light. Photoageing is thus also known as ageing of the skin, particularly of the face, ears, neck and hands, caused by UVA and UVB rays. Notably, photoageing is distinct from sunburn, which is damage caused by acute exposure of the skin to UVB. Sunburn is an acute inflammatory process and is evident visually as erythema and is characterized histologically by a mixed dermal neutrophilic and lymphocytic infiltrate. Notably, sunburn is associated with neutrophil accumulation in the dermis, which does not occur in photoaged skin.

Dry and/or scaling skin is one of the most common signs of ageing skin. Although certain individuals are more susceptible to dry and/or scaling skin, the appearance of dry and/or scaling skin can affect anyone, regardless of age, gender, or skin type.

Dry skin occurs when the skin's outer layer (the *Stratum corneum* with the *Stratum lucidum*) is depleted of water, i.e. via trans-epidermal water loss (TEWL). When this layer is well-moistened, it minimizes water loss through the skin and helps keep out irritants, allergens, and germs. However, when the *Stratum corneum* dries out, its protective function is reduced. This allows greater water loss, leaving skin vulnerable to environmental factors.

Ideally the *Stratum corneum* has a water content of 10% to 30%. This water imparts to the skin its soft, smooth, and flexible texture, i.e. the characteristics associated with the youthful appearance of skin. The water comes from the atmosphere, the underlying layers of skin, and sweat. Oil produced by skin glands and fatty substances produced by skin cells act as natural moisturizers, allowing the *Stratum corneum* to seal in water.

The body continuously loses water from the skin's surface by evaporation (TEWL). Under normal conditions, the rate of loss is slow, and the water is adequately replaced. Characteristic signs and symptoms of dry skin occur when the water loss exceeds the water replacement, and the *Stratum corneum's* water content falls below 10%.

Moisturizers which improve or eradicate dry and/or scaling skin, thereby improving the cosmetic appearance of skin (e.g. radiance or glow, skin firmness and/or skin roughness) are highly desirable. Whilst many moisturizers are known in the art, there remains a need for natural products which are effective yet gentle. Epidermal cells exhibiting an undesired or excessive pigmentation, i.e. hyper-pigmentation, e.g. liver spots, is another common sign of ageing skin. Traditionally exfoliation may be used to remove epidermal cells that are detrimental to the cosmetic appearance of skin.

Exfoliation removes the outer strata of epidermis to reveal the newer skin cells beneath. Exfoliation may be achieved by physical means (i.e. abrasion of the skin) or by chemical means. Chemical exfoliants include scrubs containing salicylic acid, glycolic acid, fruit enzymes, citric acid or malic acid and may be applied in high concentrations by a dermatologist, or in lower concentrations in over-the-counter products. Chemical exfoliation may involve the use of products that contain alpha hydroxy acids (AHAs) or beta hydroxy acids (BHAs), or enzymes that act to loosen the glue-like substances that hold the cells together at cell junctions, allowing them to ease away. This type of exfoliation is recommended for people treating acne.

The greatest disadvantage to exfoliation is the high price of some of the products and methods used to achieve it. Exfoliation will lead to some initial redness to the skin. Near the end of chemical peels, the skin will frost, with colours varying from a bright white to grey on the skin surface.

Hence, effective methods to reduce hyperpigmentation of skin, which are gentler on the skin than exfoliation, are therefore desirable.

There thus remains a need for treatments suitable for promoting the aesthetic appearance of skin. In other words, compositions and methods of improving the cosmetic appearance of skin are desirable. In particular, there is a demand for compositions and methods for restoring the youthful appearance to aged skin and/or combating the signs of ageing skin.

Compositions comprising high concentrations of an extract from *Inonotus obliquus* (Chaga), have surprisingly now been found to be remarkably effective at improving the cosmetic appearance of skin, particularly skin texture, and in reducing the physical signs associated with ageing skin, such as fine lines, wrinkles and hyperpigmentation.

*Inonotus obliquus*, commonly known as the chaga fungus or mushroom, wild Nordic Chaga fungus or Arctic Căga, is a rare species of parasitic fungus which grows on the bark of trees in the *Betula* genus, e.g. birch, and it is typically found at Northern latitudes.

Chaga has been used in folk remedies in Russia and other North-European countries for centuries. The fungus is traditionally grated or ground into a fine powder and used to brew a beverage resembling coffee or tea. However, various extracts of chaga have been used in medicine, particularly for the treatment of cancer. For instance, specific components, such as sterols, polysaccharides and terpenoids, purified from chaga have been shown to have anti-cancer/anti-tumour activities. Ergosterol peroxide from chaga mushroom exhibits anti-cancer activity by down-regulation of the β-catenin pathway in colorectal cancer (J Ethnopharmacol. 2015 Jul. 22. pii: S0378-8741(15) 30047-7). Lanostane-type triterpenes, such as 36-hydroxy-25,26,27-trinor-lanosta-8,22E-dien-24-oic acid exhibit strong cytotoxicity against A549 tumour cell lines (Fitoterapia. 2015 March; 101:34-40). Another study showed that a polysaccharide extract from the chaga mushroom can inhibit the proliferation of human neurogliocytoma cells by down-regulation of Bcl-2 and up-regulation of caspase-3 (Int J Med Mushrooms. 2014; 16(1):29-36). Thus, it is evident that chaga mushrooms represent a rich source of bio-active compounds, particularly compounds that inhibit cell proliferation.

The present inventors have unexpectedly determined that compositions for topical application to the skin containing high amounts of chaga extract are particularly effective in reducing, and even completely suppressing, UV-induced skin thickening and wrinkle formation. Notably, the effects of the chaga extract containing compositions were comparable to that of high concentration retinol.

Whilst not wishing to be bound by theory, it is hypothesised that the complex mixture of polysaccharides, beta-glucans and polyphenols in the chaga extract in the composition acts to reduce oxidative damage associated with UV damage and simultaneously improves the performance of existing keratinocytes and increases proliferation of keratinocytes in the epidermal layer of the skin. The result of these activities is a significant increase in epidermal volume and improvement in skin smoothness (i.e. a decrease in skin roughness). These results were particularly surprising in view of the high concentrations of chaga extract in the composition and the data showing that various bio-active compounds in chaga extracts actively inhibit cell proliferation.

Accordingly, at its broadest, the invention can be seen to provide a composition comprising a chaga extract as described herein for use in, or in methods for, promoting the aesthetic appearance of skin. In other words, the composition as described herein is for use in, e.g. in methods for, improving the cosmetic appearance of skin. In a particularly preferred aspect, the invention may be seen as providing compositions as described herein for use in, or in methods for, restoring the youthful appearance to aged skin and/or combating the signs of ageing skin.

Thus, in one aspect the invention provides a cosmetic composition comprising:

(i) a chaga extract at a concentration of at least about 2.5 mg/ml; and (ii) one or more physiologically or pharmaceutically acceptable excipients and/or diluents.

The chaga extract for use in the composition of the invention may be provided as a solid (e.g. a powder) that is soluble in water, e.g. at least 70, 75, 80, 85, 90 or 95%, preferably at least 96, 97, 98 or 99% (e.g. 99.9%) soluble in water. Thus, in some embodiments the invention provides a cosmetic composition in which a chaga extract solid (e.g. powder) has been dissolved in one or more physiologically or pharmaceutically acceptable excipients and/or diluents at a concentration of at least about 2.5 mg/ml.

In some embodiments, the chaga extract for use in the composition of the invention may be insoluble or partially soluble in the pharmaceutically acceptable excipients and/or diluents in the composition, e.g. less than 60, 50, 40, 30 or 25% soluble in the pharmaceutically acceptable excipients and/or diluents, e.g. less than 20, 15, 10 or 5% soluble in the pharmaceutically acceptable excipients and/or diluents. Alternatively viewed, in some embodiments, the chaga extract for use in the composition of the invention may have low solubility in water or a pharmaceutically acceptable excipient and/or diluent, e.g. the chaga extract may be at least 5%, such as at least 10, 15, 20 or 25% soluble in water or a pharmaceutically acceptable excipient and/or diluent. Accordingly, in some embodiments, the composition comprises a suspension of chaga extract at the concentrations disclosed herein. In still further embodiments, the composition may comprise a suspension and solution of the chaga extract at the concentrations disclosed herein, e.g. where a portion of the chaga extract is soluble in the pharmaceutically acceptable excipients and/or diluents of the composition and the remaining extract is insoluble, i.e. forming a suspension.

In some embodiments, the composition may comprise a chaga extract (e.g. powder, e.g. soluble, partially soluble or insoluble powder) at a concentration of at least about 3.0, 3.5, 4.0, 4.5 or 5.0 mg/ml, e.g. at least about 7.5, 10, 12.5, 15 or 20 mg/ml. In some embodiments, the composition may comprise a chaga extract at a concentration of at least about 25, 30, 35, 40, 45 or 50 mg/ml, such as at least about 60, 70, 80, 90 or 100 mg/ml, e.g. 2.5-100, 3.0-90, 3.5-80, 4.0-70, 4.5-60 or 5.0-50 mg/ml. Alternatively viewed, the chaga extract (e.g. powder) may form at least about 0.25% (w/v) of the cosmetic composition (i.e. about 0.25 g of chaga extract (e.g. powder) dissolved and/or suspended in 100 ml of cosmetic composition). Accordingly, in some embodiments the chaga extract may form at least about 0.30, 0.35, 0.40, 0.45 or 0.50% (w/v) of the cosmetic composition. Thus, in some embodiments, the chaga extract may form at least about 0.60, 0.70, 0.80, 0.90 or 1.0% (w/v) of the cosmetic composition, e.g. 0.25-1.0, 0.30-0.9, 0.35-0.8, 0.40-0.7, 0.45-0.6 or 0.50-5.0% (w/v).

As noted above, chaga extracts contain a mixture of compounds including polysaccharides, e.g. β-glucans, and polyphenols. Thus, the chaga extract for use in the composition of the invention may be defined further based on its content of β-glucans and polyphenols.

The term "β-glucans" refers to a group of β-D-glucose polysaccharides that occur naturally in the cell walls of various organisms, including fungi. Typically, β-glucans form a linear backbone with 1-3 β-glycosidic bonds but vary with respect to molecular mass, solubility, viscosity, branching structure, and gelation properties. β-glucans can be quantified using various spectrophotometric methods known in the art. For instance, a fluorescence microassay based on aniline blue dye (triphenylmethane dye), which binds specifically to 1,3β-glucan (particularly the benzophenone fluorochrome found in the dye mixture), may be used to quantify the β-glucan content of the chaga extract and/or cosmetic composition. By way of example, the method of quantifying β-glucans in the chaga extract or composition may comprise the steps of:

1. preparing or providing the dye mix (e.g. a mixture containing 40 volumes of 0.1% aniline blue in water, 21 volumes of 1 M HCl and 59 volumes of 1 M glycine/NaOH buffer pH 9.5);

2. preparing or providing a diluted sample (e.g. solution of chaga extract or composition) or control (e.g. a sample of curdlan at a known concentration), e.g. 10-50-fold with 1 M NaOH to a final volume of 300 µL in a 1.5 mL microcentrifuge tube;

3. adding NaOH to the diluted sample in step 2 (e.g. 30 µL of 6 M NaOH);

4. incubating the solution from step 3 at 80° C. for 30 minutes followed by immediate immersion on ice (e.g. in an ice bath);

5. adding the dye mix from step 1 (e.g. 630 µL) to the solution from step 4 and mixing;

6. incubating the solution from step 5 at 50° C. for 30 minutes followed by incubation at room temperature for 30 minutes (to decolourize unbound fluorescent dye);

7. measuring the fluorescence intensity of the solution from step 6 with a fluorescence spectrophotometer using an emission wavelength of 502 nm (20 nm slit width) and an excitation wavelength of 398 nm (20 nm slit width); and 8. comparing the fluorescence intensity of the sample containing chaga extract or the composition of the invention to a standard curve, e.g. produced using known concentrations of curdlan (a linear beta-1,3-glucan produced by non-pathogenic bacteria such as *Agrobacterium biobar*).

Thus, in some embodiments, the β-glucans form about at least 1% (w/w) of the chaga extract solid (e.g. powder) for use in the composition of the invention. In some embodiments, the β-glucans form at least about 2, 3, 4, 5, 6, 7, 8, 9 or 10% (w/w) of the chaga extract solid (e.g. powder) for use in the composition of the invention. Thus, in some embodiments, the β-glucans form at least about 11, 12, 13, 14, 15, 16, 17, 18, 19, 20, 21, 22, 23, 24 or 25% (w/w) of the chaga extract solid (e.g. powder) for use in the composition of the invention, e.g. about 1-35%, 2-30%, 3-25%, 4-20%, 5-15% or 5-10% (w/w) of the chaga extract solid (e.g. powder) for use in the composition of the invention, such as about 1-15% (w/w).

Accordingly, in some embodiments, the cosmetic composition of the invention may comprise β-glucans (i.e. a total amount of β-glucans) at a concentration of at least about 0.025 mg/ml. Thus, in some embodiments, the cosmetic composition of the invention may comprise β-glucans (i.e. a total amount of β-glucans) at a concentration of at least about 0.030, 0.035, 0.040, 0.045 or 0.050 mg/ml, e.g. at least about 0.075, 0.100, 0.125, 0.150 or 0.200 mg/ml. In some embodiments, the composition may comprise β-glucans (i.e. a total amount of β-glucans) at a concentration of at least about 0.045, 0.050, 0.060, 0.065 or 0.080 mg/ml, e.g. at least about 0.125, 0.165, 0.210, 0.250 or 0.350 mg/ml. In yet further embodiments, the composition may comprise β-glucans (i.e. a total amount of β-glucans) at a concentration of at least about 0.45, 0.50, 0.60, 0.65, 0.75, 0.80 or 0.85 mg/ml, such as at least about 1.0, 1.25, 1.50, 1.75 or 2.0 mg/ml. Thus, in some embodiments, the composition may comprise β-glucans (i.e. a total amount of β-glucans) at a concentration of about 0.025-2.0 mg/ml, e.g. 0.030-1.9, 0.035-1.8, 0.040-1.7, 0.045-1.6, 0.050-1.5, 0.060-1.4, 0.065-1.3, 0.070-1.2, 0.075-1.1, 0.080-1.0, 0.085-0.9, 0.090-0.8, 0.095-0.7, 0.10-0.6 or 0.125-0.5 mg/ml.

In some embodiments, the cosmetic composition of the invention may comprise β-glucans (i.e. a total amount of β-glucans) at a concentration of at least about 0.375 mg/ml. Thus, in some embodiments, the cosmetic composition of the invention may comprise β-glucans (i.e. a total amount of β-glucans) at a concentration of about at least about 0.450, 0.525, 0.600, 0.675 or 0.750 mg/ml, e.g. at least about 1.125, 1.500, 1.875, 2.250 or 3.000 mg/ml. In some embodiments, the composition may comprise β-glucans (i.e. a total amount of β-glucans) at a concentration of at least about 0.625, 0.750, 0.875, 1.000 or 1.250 mg/ml, e.g. at least about 1.875, 2.500, 3.125, 3.750 or 5.000 mg/ml. In yet further embodiments, the composition may comprise β-glucans (i.e. a total amount of β-glucans) at a concentration of at least about 6.25, 7.5, 8.75, 10, 11.25 or 12.5 mg/ml, such as at least about 15, 17.5, 20, 22.5 or 25 mg/ml. Thus, in some embodiments, the composition may comprise β-glucans (i.e. a total amount of β-glucans) at a concentration of about 0.375-25 mg/ml, e.g. 0.4-24, 0.5-23, 0.6-22, 0.7-21, 0.8-20, 0.9-19, 1.0-18, 1.2-17, 1.5-16, 1.75-15, 2-14, 3-13, 2-12, 3-11 or 4-10 mg/ml, such as 0.5-10, 0.75-9, 1-8, 1.25-7 or 1.5-6 mg/ml.

Alternatively viewed, the β-glucans (i.e. a total amount of β-glucans) may form at least about 0.0025% (w/v) (i.e. about 0.0025 g of β-glucans dissolved and/or suspended in 100 ml of cosmetic composition) of the cosmetic composition of the invention. Thus, in some embodiments, the cosmetic composition of the invention may comprise β-glucans (i.e. a total amount of β-glucans) at a concentration of at least about 0.0030, 0.0035, 0.0040, 0.0045 or 0.0050% (w/v), e.g. at least about 0.0075, 0.0100, 0.0125, 0.0150 or 0.0200% (w/v). In some embodiments, the composition may comprise β-glucans (i.e. a total amount of β-glucans) at a concentration of at least about 0.0045, 0.0050, 0.0060, 0.0065 or 0.0080% (w/v), e.g. at least about 0.0125, 0.0165, 0.0210, 0.0250 or 0.0350% (w/v). In yet further embodiments, the composition may comprise β-glucans (i.e. a total amount of β-glucans) at a concentration of at least about 0.045, 0.050, 0.060, 0.065, 0.075, 0.080 or 0.085% (w/v), such as at least about 0.10, 0.125, 0.150, 0.175 or 0.20% (w/v). Thus, in some embodiments, the composition may comprise β-glucans (i.e. a total amount of β-glucans) at a concentration of about 0.0025-0.20% (w/v), e.g. 0.003-0.19, 0.0035-0.18, 0.004-0.17, 0.0045-0.16, 0.0050-0.15, 0.0060-0.14, 0.0065-0.13, 0.0070-0.12, 0.0075-0.11, 0.0080-0.10, 0.0085-0.09, 0.0090-0.08, 0.0095-0.07, 0.010-0.06 or 0.0125-0.05% (w/v).

Thus, in still further embodiments, the β-glucans (i.e. a total amount of β-glucans) may form at least about 0.0375% (w/v) (i.e. about 0.0375 g of β-glucans dissolved in 100 ml of cosmetic composition) of the cosmetic composition of the invention. Thus, in some embodiments, the cosmetic composition of the invention may comprise β-glucans (i.e. a total amount of β-glucans) at a concentration of at least about 0.0450, 0.0525, 0.0600, 0.0675 or 0.750% (w/v), e.g. at least about 0.1125, 0.1500, 0.1875, 0.2250 or 0.3000% (w/v). In some embodiments, the composition may comprise β-glucans (i.e. a total amount of β-glucans) at a concentration of at least about 0.0625, 0.0750, 0.0875, 0.1000 or 0.1250% (w/v), e.g. at least about 0.1875, 0.2500, 0.3125, 0.3750 or 0.5000% (w/v). In yet further embodiments, the composition may comprise β-glucans (i.e. a total amount of β-glucans) at a concentration of at least about 0.625, 0.75, 0.875, 1.0, 1.125 or 1.25% (w/v), such as at least about 1.5, 1.75, 2.0, 2.25 or 2.5% (w/v). Thus, in some embodiments, the composition may comprise β-glucans (i.e. a total amount of β-glucans) at a concentration of about 0.0375-2.5% (w/v), e.g. 0.04-2.4, 0.05-2.3, 0.06-2.2, 0.07-2.1, 0.08-2.0, 0.09-1.9, 0.10-1.8, 0.12-1.7, 0.15-1.6, 0.175-1.5, 0.2-1.4, 0.3-1.3, 0.2-1.2, 0.3-1.1 or 0.4-1.0% (w/v), such as 0.05-1.0, 0.075-0.9, 0.1-0.8, 0.125-0.7 or 0.15-0.6% (w/v).

The term "polyphenols" (also known as polyhydroxyphenols or polyphenolics) refers to a structural class of organic chemicals characterized by the presence of large multiples of phenol structural units. Polyphenols are derived from the shikimate/phenylpropanoid and/or the polyketide pathway and feature more than one phenolic unit and do not contain nitrogen-based functions. Generally, polyphenols may be viewed as moderately water-soluble compounds with a typical molecular weight of about 500-4000 Da, comprising at least 12 phenolic hydroxyl groups and about 5-7 aromatic rings per 1000 Da.

The total polyphenolic content of a sample, e.g. a chaga extract or composition of the invention, can be quantified using various methods known in the art. For instance, a simple and inexpensive method used to rapidly assess the total phenolics in a sample is based on interactions of phenolics with Fast Blue BB diazonium salt in alkali pH, forming azo complexes, with the absorbance measured at 420 nm after 60 minutes. The phenolic content of a sample may be assessed relative to a standard curve measured using known concentrations of gallic acid. Thus, the total polyphenolic content of the chaga extract solid or composition of the invention may be determined by the Fast Blue BB method described above. Accordingly, unless specified otherwise, the polyphenolic content of the chaga extract or composition disclosed herein are expressed as gallic acid equivalents. Thus, in some embodiments, polyphenolics (polyphenols) form at least about 0.10% (w/w) of the chaga extract solid (e.g. powder) for use in the composition of the invention. In some embodiments, polyphenolics form at least about 0.15, 0.20, 0.25, 0.30, 0.35, 0.40, 0.45 or 0.50% (w/w) of the chaga extract solid (e.g. powder) for use in the composition of the invention. For instance, polyphenolics may form at least about 0.6, 0.7, 0.8, 0.9, 1.0, 1.1, 1.2, 1.3, 1.4, 1.5, 1.75 or 2.0% (w/w) of the chaga extract solid (e.g. powder) for use in the composition of the invention. Thus, for instance, polyphenolics may form about 0.10-2.0.%, 0.15-1.75%, 0.20-1.5, 0.25-1.4, 0.30-1.3, 0.35-1.2, 0.40-1.1 or 0.5-1.0% (w/w) of the chaga extract solid (e.g. powder) for use in the composition of the invention.

Thus, in some embodiments, polyphenolics (polyphenols) form at least about 2.5% (w/w) of the chaga extract solid (e.g. powder) for use in the composition of the invention. In some embodiments, polyphenolics form at least about 3.0, 3.5, 4.0, 4.5 or 5.0% (w/w) of the chaga extract solid (e.g. powder) for use in the composition of the invention, e.g. about 2.5-5.0%, 3.0-4.5% or 3.5-4.0% (w/w) of the chaga extract solid (e.g. powder) for use in the composition of the invention, such as about 4.0-5.0% (w/w).

Accordingly, in some embodiments, the cosmetic composition of the invention may comprise polyphenolics (i.e. total polyphenolic content) at a concentration of at least about 0.0030 mg/ml (gallic acid equivalents). Thus, in some embodiments, the cosmetic composition of the invention may comprise polyphenolics (i.e. a total polyphenolic content) at a concentration of at least about 0.0035, 0.0040, 0.0045 or 0.0050 mg/ml, e.g. at least about 0.006, 0.007, 0.008, 0.009 or 0.010 mg/ml. In some embodiments, the composition may comprise polyphenolics (i.e. the total polyphenolic content) at a concentration of at least about 0.0125, 0.0150, 0.0175, 0.0200 or 0.0250 mg/ml, e.g. at least about 0.0375, 0.0500, 0.0625, 0.0750 or 0.100 mg/ml. In yet further embodiments, the composition may comprise polyphenolics (i.e. a total polyphenolic content) at a concentration of at least about 0.125, 0.150, 0.175, 0.200, 0.225 or 0.250 mg/ml, such as at least about 0.30, 0.35, 0.40, 0.45 or 0.50 mg/ml. Thus, in some embodiments, the composition may comprise polyphenolics (i.e. a total polyphenolic content) at a concentration of about 0.0030-0.50 mg/ml, e.g. 0.0035-0.45, 0.0040-0.40, 0.0045-0.35, 0.0050-0.30, 0.006-0.250, 0.007-0.225, 0.008-0.200, 0.009-0.175, 0.010-0.150, 0.0125-0.125, 0.0150-0.100, 0.0175-0.075, 0.020-0.0625 or 0.025-0.05 mg/ml.

Thus, in some embodiments, the cosmetic composition of the invention may comprise polyphenolics (i.e. total polyphenolic content) at a concentration of about at least 0.075 mg/ml (gallic acid equivalents). Thus, in some embodiments, the cosmetic composition of the invention may comprise polyphenolics (i.e. a total polyphenolic content) at a concentration of at least about 0.090, 0.105, 0.120, 0.135 or 0.150 mg/ml, e.g. at least about 0.225, 0.300, 0.375, 0.450 or 0.600 mg/ml. In some embodiments, the composition may comprise polyphenolics (i.e. the total polyphenolic content) at a concentration of at least about 0.125, 0.150, 0.175, 0.200 or 0.250 mg/ml, e.g. at least about 0.375, 0.500, 0.625, 0.750 or 1.000 mg/ml. In yet further embodiments, the composition may comprise polyphenolics (i.e. a total polyphenolic content) at a concentration of at least about 1.25, 1.5, 1.75, 2.0, 2.25 or 2.5 mg/ml, such as at least about 3.0, 3.5, 4.0, 4.5 or 5.0 mg/ml. Thus, in some embodiments, the composition may comprise polyphenolics (i.e. a total polyphenolic content) at a concentration of about 0.075-5.0 mg/ml, e.g. 0.08-4.8, 0.1-4.6, 0.12-4.4, 0.14-4.2, 0.16-4.0, 0.18-3.8, 0.20-3.6, 0.22-3.4, 0.24-3.2, 0.35-3.0, 0.4-2.8, 0.6-2.6, 0.4-2.4, 0.6-2.2 or 0.8-2.0 mg/ml, such as 0.1-2.0, 0.15-1.8, 0.20-1.6, 0.25-1.4 or 0.3-2.0 mg/ml.

Alternatively viewed, the polyphenolics (i.e. a total polyphenolic content) may form at least about $7.5 \times 10^{-3}$% (w/v) (i.e. about 0.0075 g of polyphenolics dissolved in 100 ml of cosmetic composition) of the cosmetic composition of the invention. Thus, in some embodiments, the cosmetic composition of the invention may comprise polyphenolics (i.e. a total polyphenolic content) at a concentration of at least about $9 \times 10^{-3}$, $10.5 \times 10^{-3}$, $12 \times 10^{-3}$, $13.5 \times 10^{-3}$ or $15 \times 10^{-3}$% (w/v), e.g. at least about $22.5 \times 10^{-3}$, $30 \times 10^{-3}$, $37.5 \times 10^{-3}$, $45 \times 10^{-3}$ or $60 \times 10^{-3}$% (w/v). In some embodiments, the composition may comprise polyphenolics (i.e. a total polyphenolic content) at a concentration of at least about $12.5 \times 10^{-3}$, $15 \times 10^{-3}$, $17.5 \times 10^{-3}$, $20 \times 10^{-3}$ or $25 \times 10^{-3}$% (w/v), e.g. at least about $37.5 \times 10^{-3}$, $50 \times 10^{-3}$, $62.5 \times 10^{-3}$, $75 \times 10^{-3}$ or $100 \times 10^{-3}$% (w/v). In yet further embodiments, the composition may comprise polyphenolics (i.e. a total polyphenolic content) at a concentration of about at least 0.125, 0.15, 0.175, 0.200, 0.225 or 0.25% (w/v), such as at least about 0.3, 0.35, 0.4, 0.45 or 0.5% (w/v). Thus, in some embodiments, the composition may comprise polyphenolics (i.e. a total polyphenolic content) at a concentration of about $7.5 \times 10^{-3}$-0.5% (w/v), e.g. $8.0 \times 10^{-3}$-0.48, 0.01-0.46, 0.012-0.44, 0.014-0.42, 0.016-0.40, 0.018-0.38, 0.02-0.36, 0.024-0.34, 0.03-0.32, 0.035-0.3, 0.04-0.28, 0.06-0.26, 0.04-0.24, 0.06-0.22 or 0.08-0.2% (w/v), such as 0.01-0.20, 0.015-0.18, 0.02-0.16, 0.025-0.14 or 0.03-0.12% (w/v).

As discussed is the Examples, the chaga extract used in the composition of the invention exhibits a very potent antioxidative effect in a skin keratinocyte model cellular antioxidative assay (CAA) analysis. Accordingly, the chaga extract and composition of the invention may be defined further by reference to their antioxidative (antioxidant) properties. In this respect, the antioxidant capacity of the chaga extract or composition may be measured using an oxygen radical absorbance capacity (ORAC) method, which measures the antioxidant capacity of a given substance, as compared to the standard, Trolox. Thus, the ORAC of a sample may be expressed in terms of µmol of Trolox equivalents (TE) per 100 g of sample.

Thus, in some embodiments, the chaga extract solid (e.g. powder) for use in the composition of the invention has an ORAC of at least about 45000 µmol TE per 100 g (of chaga extract). In some embodiments, the chaga extract solid (e.g. powder) for use in the composition of the invention has an ORAC of at least about 47500, 50000, 52500, 55000, 57500 or 60000 µmol TE per 100 g, e.g. about 45000-75000, 50000-70000 or 55000-65000 µmol TE per 100 g.

Alternatively viewed, in some embodiments, the composition of the invention has an ORAC of at least about 1.125 µmol TE per ml of composition. Thus, in some embodiments, the composition of the invention has an ORAC of at least about 1.250, 1.375 or 1.500 µmol TE per ml of composition. In some embodiments, the composition of the invention has an ORAC of at least about 22.5, 27.5, 30.0, 35.0, 40.0 or 45.0 µmol TE per ml of composition, e.g. about 1.125-45.0, 1.125-40.0, 1.375-35.0 or 1.500-30.0 µmol TE per ml of composition, such as about 1.125-27.5, 1.5-25, 2-22.5, 2.5-20, 3-15 µmol TE per ml of composition. It will be evident that the ORAC values given above are illustrative of the ranges that may be present in the composition of the invention. In this respect, the ORAC of the composition of the invention may be calculated based on the values listed above with respect to the chaga extract for use in the composition and the values disclosed herein relating to the amount of extract present in the composition.

The chaga extract for use in the composition may be produced by any suitable means and various methods are known in the art. In some embodiments, the chaga extract is prepared using a hot water extraction method. For instance, the chaga extract for use in the composition of the invention may be obtained or obtainable by a method comprising the steps of:

1) providing chaga mushroom dry matter, e.g. milled or ground chaga mushroom that has been dried;

2) contacting water with the chaga mushroom dry matter of step 1) and incubating the resultant suspension, preferably at a temperature in excess of about 60° C., for at least about 1 hour, preferably at least 2, 3 or 4 hours;

3) removing solids (insoluble matter) from the suspension obtained from step 2), e.g. by filtration or centrifugation, to obtain a chaga extract solution;

4) optionally sterilizing the chaga extract solution from step 3), e.g. by filter sterilization; and 5) producing a solid (e.g. dry powder) from the chaga extract solution of step 3) or 4), e.g. by spray-drying, freeze-drying, microencapsulation etc.

The chaga mushroom dry matter may be obtained from any suitable source of chaga mushrooms. For instance, the chaga mushrooms may be obtained from a natural source, e.g. harvested from birch trees, or an artificial source, e.g. the chaga mushrooms may be grown, cultured or cultivated in artificial conditions, such as on or in a growth medium in an incubator.

The temperature of the extraction process in step 2) is preferably in the range of 60–100° C., 65-95° C., 70-90° C. or 75-85° C., e.g. about 80° C. Accordingly, it will be understood that in practice the reaction may be carried out under high pressure, e.g. at least about 2, 3 or 4 MPa. Advantageously, performing the extraction method under high pressure may prevent the degradation of bioactive β-glucans.

By high pressure is meant the reaction is performed in a suitable pressure proof reactor, for example the IMR E-400 mixer-reactor manufactured by Lipp Mischtechnik GmbH, Mannheim, Germany, however the skilled person would be able to select an appropriate reactor without undue burden. The extraction process may take place under pressure conditions which are determined by the temperature of the reaction. The relationship between pressure and temperature is well known in the art and data tables reciting the pressure observed at a corresponding temperature are available, e.g. CRC Handbook of Chemistry and Physics (91st edition, 2010 Ed. Haynes, W. M, CRC Press). Generally pressure is increased to temperature or vice versa.

Typically, water is added to an approximate dry matter content of 1-20%, and more generally the dry matter content of the starting chaga mushroom solution/suspension may range between 2-15%, or more particularly 3-14%, preferably 4-12%, most preferably 5-10%.

The increased temperatures may be reached in any number of ways, which will be known in the art, including but not limited to, indirectly through the pressure reactor jacket or by steam injection directly into the reactor.

The extraction reaction is generally maintained under constant temperature and pressure conditions as contemplated above, for a minimum of 1 hour. Typically the extraction process will proceed for 1-10 hours, preferably 2-8, 3-7, 4-6 and most preferably 4-5 hours.

The step of removing solids, i.e. insoluble material, from the extract may be achieved by any suitable means known in the art. For instance, in some embodiments, the step of removing the solids may comprise a step of filtering the suspension from step (2) using a filter with a pore size of 0.30-0.60 µm, preferably a pore size of 0.35-0.55, particularly preferably 0.40-0.50 µm, most preferably 0.45 µm, and collecting the filtrate, which forms the chaga extract solution. In other embodiments, the step of removing the solids may comprise a step centrifuging the suspension from step (2), e.g. at 10,000 g for at least about 20 minutes.

In some embodiments, it may be desirable or advantageous to sterilize the chaga extract solution to reduce the bio-burden. This may be achieved by filter sterilizing the solution. This is preferably achieved by filtering the solution through a 0.2-0.45 µm filter. Thus, in some embodiments, the steps of removing insoluble material and sterilizing the solution may be performed simultaneously.

The step of producing a solid (e.g. dry powder) from the chaga extract solution of step 3) or 4), i.e. the step of dehydrating the chaga extract solution, may be achieved by numerous techniques well known to the skilled person, and preferably by spray-drying. In some embodiments, it may be preferable or advantageous to encapsulate the chaga extract, e.g. using standard microencapsulation techniques well-known in the art. For instance, the chaga extract solution may be mixed with solution of maltodextrin (with a dextrose equivalent (DE) value of at least about 5, e.g. about 5-20, 6-18, 7-16, 8-14, 9-12, such as about 10), e.g. in a 1:1 ratio, and subsequently spray-dried. The resultant powder, which may be a microencapsulated form of the chaga extract, may be used to produce the cosmetic composition of the invention. In some embodiments, the powder may be sieved to generate a homogenous particle size prior to its incorporation in a cosmetic composition to facilitate its uniform dissolution or distribution in the composition at the concentration described above.

Thus, the chaga extract for use in the composition of the invention is not a fermented chaga extract or an extract thereof.

A "fermented chaga extract" refers to an extract obtained by culturing chaga mycelia in a fermentation medium (e.g. comprising a carbon and/or nitrogen source) for a period of time, e.g. days, under conditions suitable to facilitate the growth of the mycelia and subsequently separating the mycelia from the fermentation medium to obtain a fermented extract. The fermented extract optionally may be further extracted to obtain an extract, e.g. a mixture of components such as exopolysaccharides, from the fermented extract.

The chaga extract solid (e.g. powder) described above may be used to produce a composition of the invention, which may be formulated in a conventional manner with one or more physiologically acceptable carriers, excipients and/or diluents, according to techniques well known in the art using readily available ingredients.

Thus, a further aspect of the invention comprises the use of the chaga extract solid (e.g. powder) described above in the formulation of a cosmetic composition comprising the chaga extract at a concentration of at least about 2.5 mg/ml and one or more physiologically or pharmaceutically acceptable excipients and/or diluents.

A further aspect of the invention provides a method of producing a cosmetic composition comprising adding a chaga extract solid (e.g. powder) described herein to one or more physiologically or pharmaceutically acceptable excipients and/or diluents, wherein the chaga extract solid is present at a concentration of at least about 2.5 mg/ml.

Additional preparation method steps include changing or modifying the pH, ion concentration etc. and/or adding one or more additional active ingredients. In some embodiments, the pH of the cosmetic composition is about 5.0-8.0, e.g. about 6.0-7-0.

By "pharmaceutically acceptable" or "physiologically acceptable" is meant that the ingredient must be suitable for cosmetic applications and compositions. The ingredient also must be compatible with other ingredients in the composition as well as physiologically acceptable to the recipient.

The composition of the invention is for topical (i.e. to the skin) administration.

Topical compositions include gels, creams, ointments, sprays, lotions, salves, sticks, soaps, powders, films, aerosols, drops, foams, solutions, emulsions, suspensions, dispersions, e.g. non-ionic vesicle dispersions, milks and any other conventional cosmetic forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

In a preferred embodiment of the invention, the composition of the invention is a liquid, preferably an aqueous solution and/or suspension.

Other pharmaceutically acceptable components or ingredients that may be added to the composition of the invention may be active components, i.e. components that have an effect on the skin, preferably that also act to promote the aesthetic appearance of skin or improve the cosmetic appearance of skin, e.g. in the cosmetic indications described herein. Thus, alternatively or additionally, the methods may comprise a further step of adding one or more pharmaceutically acceptable active components to the composition or combining the composition with one or more pharmaceutically acceptable active components.

Pharmaceutically acceptable active components may include minerals, vitamins, enzymes, proteins, peptides, amino acids, lipids, antioxidants, polysaccharides, substances suitable as sunscreen filters, chemical exfoliants, extracts and mixtures thereof, as described in more detail below.

In some embodiments the composition of the invention contains one or more vitamins. Vitamins may be selected from, but are not limited to, any one or more of vitamin A and derivatives thereof (e.g. retinoid or retinol or their derivatives such as retinyl palmitate or retinyl proprionate), biotin, folic acid, calcium pantothenate, nicotinamide, pyridoxine HCl, pyridoxal HCl, riboflavin, thiamine HCl, thymidine, vitamin B12, vitamin B3 (e.g. niacinamide), vitamin B5 (e.g. panthenol), vitamin C and derivatives thereof (e.g. ascorbyl palmitate, Na ascorbyl phosphate, Mg ascorbyl phosphate, ascorbyl acetate), tocopherols and derivatives (e.g. vitamin E acetate).

In some embodiments, the composition of the invention comprises vitamin C or a derivative thereof. In particularly preferred embodiments, the composition comprises sodium ascorbyl phosphate.

Additionally or alternatively, in some embodiments, the composition of the invention comprises vitamin E or a derivative thereof, e.g. tocopherol acetate, and/or vitamin B5 or a derivative thereof, e.g. panthenol.

In still further embodiments, the composition of the invention may contain coenzyme Q10 (also known as ubicuinona).

Thus, in a particularly preferred aspect the invention provides a composition comprising:
(i) a chaga extract at a concentration of at least about 2.5 mg/ml;
(ii) vitamin C or a derivative thereof, e.g. sodium ascorbyl phosphate;
(iii) vitamin E or a derivative thereof, e.g. tocopherol acetate;
(iv) vitamin B5 or a derivative thereof;
(v) coenzyme Q10; and
(vi) one or more physiologically or pharmaceutically acceptable excipients and/or diluents.

In some embodiments, the composition may contain effective amounts of one or more agents to stabilize the chaga extract (or components of the chaga extract, e.g. polyphenolics and/or β-glucans) against degradation. Additionally or alternatively, the composition may comprise effective amounts of one or more preservatives or anti-microbials to prevent the spoilage of the composition.

Stabilizing agents, preservatives and anti-microbials suitable for use in cosmetic compositions are well-known in the art and include, for example, salts or non-electrolytes, acetate, SDS, EDTA, citrate or acetate buffers, mannitol, glycine, polysorbate, benzyl alcohol, urea.

The composition may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, fragrance, ionic or non-ionic thickeners, surfactants, filler, ionic or non-ionic thickener, sequestrant, polymer, propellant, alkalinizing or acidifying agent, opacifier, colouring agents and fatty compounds and the like. Some of these components are described in more detail below.

Examples of proteins that may be combined with the composition of the invention include collagen and/or a derivative thereof (e.g. portions thereof), a protein or peptide which is capable of promoting cell growth, glycoprotein 1, glycoprotein 2 and laminin.

The composition of the invention may be combined with enzymes including, but not limited to, any one or more of, fruit enzymes (e.g. bromelain), superoxide dismutase, peroxidase, hyaluronidase and mucopolysaccharidase.

Peptides may be selected from, but are not limited to, any one or more of D,L-carnosine, D-carnosine, L-carnosine, anserine and Matrixyl (pentapeptide derivative).

Amino acids may be selected from, but not limited to, any one or more of L-alanine, L-arginine, L-asparagine, L-aspartic acid, L-cysteine, L-cystine, glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine, and L-valine and derivatives thereof including non-naturally occurring amino acids as defined in Table 1. Particularly preferred amino acids as antioxidants may be selected from any one or more of glycine, lysine, arginine, cysteine, cystine, histidine, tyrosine and tryptophan.

The cosmetic composition may comprise one or more lipids which include fats, oils, waxes and the like. Suitable polar oils are, for example, those from the group of lecithins and fatty acid triglycerides, namely the triglycerol esters of saturated and/or unsaturated, branched and/or unbranched alkanecarboxylic acids with a chain length of from 8 to 24, in particular 12 to 18, carbon atoms. The fatty acid triglycerides can, for example, be chosen advantageously from the group of synthetic, semisynthetic and natural oils, such as, for example, olive oil, sunflower oil, soya oil, peanut oil, rapeseed oil, almond oil, palm oil, coconut oil, castor oil, wheat germ oil, grape seed oil, thistle oil, evening primrose oil, macadamia nut oil and the like.

Alternatively or additionally the oil may be selected from volatile oils, non-volatile oils or mixtures thereof. Non-volatile oils include oils that fulfill at least one of the following definitions: (a) the oil exhibits a vapour pressure of no more than 0.2 mm Hg at 25° C. and one atmosphere pressure; (b) the oil has a boiling point at one atmosphere of at least 300° C. Volatile oils include materials that are not "non-volatile" as defined above.

Non-volatile oils may be selected from non-volatile silicone oils, non-volatile hydrocarbon oils and mixtures thereof. Suitable non-volatile silicone oils include linear polymethylsiloxanes and, preferably, non-volatile silicone oils are high molecular weight dimethicones.

Suitable non-volatile hydrocarbon oils include branched esters of diglycerin or triglycerin or the esters or 1,2,3,4 butane triol or erythritol, di erythritol or tri erthyritol. Preferably, non-volatile hydrocarbon oils comprise erythrityl triethylhexanoate and Polyglyceryl-2 triisostearate, diethyl hexyl carbonate, dicapryl Ether, dicapryl Carbonate, isononyl isononanoate, tridecyl Neopentanoate, or a mixture thereof.

Volatile oils may be selected from volatile silicone oils, both functionalised and non-functionalised, volatile hydrocarbon oils and mixtures thereof. Volatile oil useful in the present invention may be saturated or unsaturated, have a straight or branched chain or a cyclic structure or have a combination of any one or more of said features.

Examples of volatile hydrocarbons oils include polydecanes such as isododecane and isodecane and the C7-C15 isoparaffins.

The volatile silicone oil may be selected from cyclopentasiloxane, cyclohexasiloxane or a mixture thereof. The linear volatile silicone oil may be a linear polymethylsiloxane.

The cosmetic composition of the invention may further comprise one or more polysaccharides selected from, but not limited to, any one or more of anionic polysaccharides (e.g. alginic acid, pectin, xanthan gum, hyaluronic acid, chondroitin sulfate, gum arabic, gum karaya, gum tragacanth, carboxymethyl-chitin, cellulose gum, glycosaminoglycans), cationic polysaccharides (e.g. chitosan, acetylated chitosan, cationic guar gum, cationic hydroxyethylcellulose (HEC)), nonionic polysaccharides (e.g. starch, dextrins, guar gum, cellulose ethers such as hydroxyethylcellulose, methylcellulose and nitrocellulose), amphoteric polysaccharides (e.g. carboxymethylchitosan, N-hydroxy-dicarboxyethyl-chitosan, modified potato starch) and hydrophobic polysaccharides (e.g. cetyl hydroxyethylcellulose, polyquaternium24).

The cosmetic composition may further comprise a substance suitable as a sunscreen filter such as an organic sunscreen, e.g. a cinnamic derivative. The organic sunscreen active may be selected from hydrophilic organic sunscreen, hydrophobic organic sunscreen, or mixtures thereof. Suitable examples of sunscreens may be found in the CTFA International Cosmetic Ingredient Dictionary and Handbook, 7th edition volume 2, pp. 1672, edited by Wenning and Mc Ewen (The Cosmetic, Toiletry, and Fragrance Association, Inc., Washington, D.C. 1997).

The organic sunscreen may be selected from alkyl β,β-diphenylacrylate derivatives, α-cyano β,β-diphenylacrylate derivatives, anthranilate derivatives, benzophenone derivatives, camphor derivatives, dibenzoylmethane derivatives, p-aminobenzoic derivatives, salicylic derivatives, triazine derivatives, or mixtures thereof. For instance the hydrophobic organic sunscreen may be selected from 4-(1,1-dimethylethyl)-4'-methoxydibenzoylmethane; 4-isopropyldibenzoylmethane; 4-(1,1-dimethylethyl)-4'-methoxydibenzoylmethane, 2-ethylhexyl-2-cyano-3,3-diphenylacrylate, or a mixture thereof.

In some embodiments the hydrophilic organic sunscreen may be 2-phenylbenzimidaole-5-sulfonic acid.

Suitable examples of cinnamic derivative sunscreens may be found in the CTFA International Cosmetic Ingredient Dictionary and Handbook, 7th edition volume 2, pp. 1672, edited by Wenning and Mc Ewen (The Cosmetic, Toiletry, and Fragrance Association, Inc., Washington, D.C. 1997). The cinnamic derivative may be selected from 2-ethylhexyl-p-methoxycinnamate, diethanolamine methoxycinnamate, 2-ethoxyethyl-p-methoxycinnamate, or a mixture thereof. For instance, the cinnamic derivative may be 2-ethylhexyl-p-methoxycinnamate.

The cosmetic composition may be combined with a chemical exfoliant selected from, but not limited to, any one more of alpha hydroxy acids (AHAs), beta hydroxy acids (BHAs) or poly-hydroxy acids, such as salicylic acid, glycolic acid, citric acid and malic acid.

Extracts that may be incorporated in the cosmetic composition include, but are not limited to plant extracts, which may comprise phenolic compounds such as, for example, flavonoids (e.g., glycosyl rutin, ferulic acid, caffeic acid), furfurylidene glucitol, butylated hydroxytoluene, butylated hydroxyanisole, nordihydroguaiaretic resin acid, nordi-hydroguaiaretic acid, trihydroxybutyrophenone and derivatives thereof. Particular plant extracts for use in the composition of the invention include aloe vera extract, ginseng extract and horsetail extract.

Ginseng extract is obtainable by extracting with a hydrophilic solvent (in particular, water, ethanol, glycol, or any mixtures thereof) the root of Panax ginseng. The extract contains saponins, sterols, carbohydrates, pectin, vitamins, minerals and lipids.

Horsetail extract is obtainable by extracting with a hydrophilic solvent (e.g., water, ethanol, glycol, or any mixtures thereof) the whole herb of Equisetum arvense. The extract contains silicates, flavinoids, saponosides, caffeic acid and ferulic acid.

In some particularly preferred embodiments, the cosmetic composition and/or chaga extract does not contain extracts of plants and/or other fungi.

For instance, in preferred embodiments, the chaga mushroom dry matter used in the method to produce the chaga extract described above does not contain matter from plants and/or other fungi, i.e. it contains only chaga mushroom dry matter or alternatively viewed consists essentially of chaga mushroom dry matter (i.e. at least 95%, preferably at least 96%, 97%, 98% or 99% chaga mushroom dry matter). Accordingly, in particularly preferred embodiments, the step of contacting water with the chaga mushroom dry matter excludes the addition of matter from plants and/or other fungi.

Thus, in some embodiments, the chaga extract solid (e.g. powder) described above used in the formulation of a cosmetic composition does not contain extracts from plants and/or other fungi.

In still further embodiments, the method of producing a cosmetic composition comprising adding a chaga extract solid (e.g. powder) described herein to one or more physiologically or pharmaceutically acceptable excipients and/or diluents, excludes the addition of extracts from plants and/or other fungi.

The term "extract" as used herein refers to a substance or composition comprising multiple compounds (i.e. a mixture of compounds) obtained by extracting a plant or fungi (or part thereof) using a solvent, such as ethanol or water. Thus, a single purified substance, compound or agent (e.g. active agent) obtained from a plant or fungi is not an extract as defined herein.

The cosmetic composition may further comprise a skin-conditioning agent. The skin-conditioning agent may be selected from humectants, exfoliants, emollients or mixtures thereof. Humectants includes polyhydric alcohols such as glycerine, propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerine or mixtures thereof.

Examples of antioxidants that may be combined with the composition of the invention include but are not limited to amino acids, vitamins, minerals, carotenoids, peptides, thiols, sulfoximine compounds, chelators, unsaturated fatty acids, phenolic compounds, plant extracts, stilbenes, uric acid, mannose, chlorogenic acid, imidazoles (e.g. urocanic acid), furfurylidenesorbitol, ubiquinone, ubiquinol, plastoquinone, phytosterols and derivatives thereof (e.g. salts, esters, ethers, sugars, nucleotides, nucleosides, peptides and/or lipid derivatives), some of which are described above.

Minerals may be selected from, but are not limited to, any one or more salts of molybdenate (e.g. $(NH_4)OMo_7O_{24}$) aluminium (e.g. $AlCl_3$), calcium (e.g. $CaCl_2$), cobalt (e.g. $CoCl_2$), chromium (e.g. $CrK(SO_4)$), copper (e.g. $CuSO_4$), iron (e.g. $Fe(NO_3)_3$, $FeSO_4$), potassium (e.g. KCl), magnesium (e.g. $MgCl_2$), manganese (e.g. $MnCl_2$, $MnSO_4$), phosphate (e.g. $Na_2HPO_4$, $NaH_2PO_4$), carbonate (e.g. $NaHCO_3$), silicate (e.g. $Na_2SiO_3$), sodium (e.g. NaCl), vanadate (e.g. $NH_4VO_3$), nickel (e.g. $NiCl_2$), tin (e.g. $SnCl_2$), zinc (e.g., ZnO, $ZnSO_4$), selenium (e.g. selenomethionine, ebselen, $H_2SeO_3$, $Na_2SeO_3$), sulphate and nitrate.

Carotenoids, may be selected from, but are not limited to, any one or more of carotenes, e.g. α-carotene, β-carotene, ψ-lycopene, phytoene etc. and derivatives thereof.

Thiols may be selected from, but are not limited to, any one or more of aurothioglucose, propylthiouracil, thioredoxin, lipoic acid, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters and the salts thereof, dilauryl thiodipropionate, distearyl thiodipropionate, thiodipropionic acid and derivatives thereof.

Sulfoximine compounds may be selected from, but are not limited to, any one or more of homocysteine sulfoximine, buthionine sulfones, penta-, hexa-, heptathionine sulfoximine, which may be included in the composition such that they are provided in very low dosages (e.g. pmol to μmol/kg).

Chelators may be selected from, but are not limited to, any one or more of apoferritin, desferral, lactoferrin, α-hydroxy fatty acids, palmitic acid, phytic acid, α-hydroxy acids (e.g. citric acid, lactic acid, malic acid), humic acid, bile acid, bile extracts, bilirubin, biliverdin, EDTA, EGTA and derivatives thereof.

Unsaturated fatty acids may be selected from, but are not limited to, any one or more of γ-linolenic acid, linoleic acid, oleic acid and derivatives thereof.

Stilbenes and derivatives thereof include, for example, stilbene oxide and trans-stilbene oxide.

A variety of additional optional active ingredients may be incorporated into the cosmetic compositions of the present invention. Non-limiting examples of these additional ingredients include additional skin care actives such as farnesol, linalool, bisabolol, phytantriol, urea, guanidine (e.g. amino guanidine); hexaminidine compounds, salts or derivatives thereof; sugar amines; self-tanning agents (e.g. dehydroxyacetone); structuring agents; hydrophilic gelling agents; anti-acne medicaments (resorcinol, salicylic acid, and the like); skin soothing and healing agents such as allantoin and the like; and agents suitable for aesthetic purposes such as essential oils, fragrances, skin sensates, opacifiers, aromatic compounds (e.g. clove oil, menthol, camphor, eucalyptus oil, and eugenol).

The compositions described herein may be formulated so as to provide quick, sustained or delayed release of the active ingredient(s) after administration to the body by employing techniques well known in the art.

The composition may be in any appropriate dosage form to allow delivery or for targeting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems.

The use of solutions, suspensions, gels and emulsions are preferred, e.g. the active ingredient may be carried in water, a water-based liquid, an oil, a gel, an emulsion, an oil-in water or water-in-oil emulsion, a dispersion or a mixture thereof.

The emulsifier may be selected from nonionic emulsifiers, anionic emulsifiers, cationic emulsifiers, zwitterionic emulsifiers, amphoteric emulsifiers or mixtures thereof. Emulsifiers are known in the art. See, e.g., McCutcheon's, Detergents and Emulsifiers, North American Edition (1986), published by Allured Publishing Corporation.

When the cosmetically acceptable carrier is a water-in-silicone emulsion, emulsifiers are preferably selected from polyoxyalkylene copolymers, polyglyceryl copolymers or mixtures thereof. Polyoxyalkylene copolymers, also known as silicone polyethers, are described in detail in U.S. Pat. No. 4,268,499.

In some embodiments the cosmetic compositions described herein may be topically administered to the skin via a product, device or material to which the composition has been applied, impregnated or chemically bonded. To this end, bandages, plasters (e.g. adhesive patches), gauze, surgical tape, cotton swabs or other absorbent materials, e.g. a puff, fleece, or sponge, or supportive matrices may be coated, impregnated or chemically bonded with a composition as described herein. For example, many compositions can be applied to the skin using dermal patches that are well described in the art, e.g. US 2008/0038300, US 2009/0043236, WO 2005/067499 and WO 2009/085302, which are incorporated herein by reference. In some embodiments, the material comprising the composition as described herein may be in the form of a device that can be, e.g. worn by the subject to be treated. For instance, the composition as described herein may be applied, impregnated or chemically bonded onto a material or supportive matrix that forms all or part of a diaper, glove, sock etc.

The cosmetic compositions can be included in a container, pack, or dispenser together with instructions for administration.

Hence, a further aspect of the invention comprises the provision of a product, material or device which is coated, impregnated or chemically bonded with composition as described herein. The invention also extends to such products, materials or devices for uses as described herein. Preferably said product is a bandage, plaster (e.g. adhesive patch), gauze, surgical tape or cotton swab or said device is a diaper, glove or sock.

As discussed above, the composition of the invention is for use in improving the cosmetic appearance of the skin of a mammalian animal.

As referred to herein "cosmetic" is intended to refer to a treatment which does not cure, treat or prevent a disease or disorder, but instead serves as a skincare product or to modify or improve the appearance of the skin, e.g. the colour, texture or moisture content of the skin.

The basis of the treatments described herein is the skin anti-ageing and keratinocyte enhancing effects of the compositions as disclosed herein. These effects have been shown in the Examples provided herein.

Thus treatments based on the anti-ageing and keratinocyte enhancing effects of the compositions described herein are contemplated.

The invention thus provides a cosmetic method of improving the appearance of skin of a mammalian animal, wherein a cosmetic composition as described hereinbefore is administered to said animal.

In a particularly preferred embodiment the skin is aged skin.

"Aged skin" refers to skin that displays one or more signs or symptoms of ageing, i.e. the appearance of wrinkles, fine lines, hyperpigmentation, laxity (sagging), dry skin, increased roughness or transepidermal water loss (TEWL). In particular, "aged skin" is determined relative to normal optimum skin, i.e. healthy, hydrated, normally pigmented and non-aged skin. In this respect, aged skin need not be related to the age of the subject and may be aged prematurely, e.g. by chronic exposure to sunlight (photo-damage). However, it will be evident that to have experienced chronic exposure to sunlight requires a subject to have been exposed to sunlight consistently, e.g. daily, for several years. Accordingly, reference to aged skin herein refers to the skin of an adult, typically an adult of at least about 25 years, e.g. at least about 30, 35 or 40 years.

Thus, the relative parameters for "normal optimum skin" may be determined as the average measurements of the above signs of ageing from a number of subjects of the same or similar age to the subject in question, e.g. subjects that have not received chronic exposure to sunlight. Alternatively, the relative parameters for "normal optimum skin" may be taken as the measurements from subjects that are younger than the subject in question. In other words, the compositions as described herein may be used to restore the youthful appearance of skin, relative to the skin of the subject at an earlier age.

Thus, in some embodiments, the composition is for improving the cosmetic appearance of chronologically-aged skin, i.e. skin that has one or more signs of ageing as a result of the age of the subject, e.g. for improving the cosmetic appearance of skin in subjects of at least 30, 35, 40 or 45 years.

In some embodiments, the composition is for improving the cosmetic appearance of photo-aged skin, i.e. skin that has one or more signs of ageing as a result of chronic exposure to sunlight, e.g. for improving the cosmetic appearance of skin in subjects that have experienced chronic exposure to sunlight for at least 5 years. Thus, in some embodiments, subjects with photo-aged skin are less than 50, e.g. less than 45, 40 or 35 years old.

In some embodiments, improving the cosmetic appearance of skin (e.g. chronologically-aged or photo-aged skin) involves a reduction or prevention in the cosmetic appearance or prevalence of wrinkles, fine lines, hyperpigmentation, laxity, dry skin, sagging (laxity), skin roughness and/or transepidermal water loss. One or more of these parameters may be improved. Preferably fine lines and/or wrinkles are reduced. Thus, alternatively viewed, improving the cosmetic appearance of skin (e.g. chronologically-aged or photo-aged skin) may involve an increase in skin hydration, smoothness, firmness and/or radiance/glow.

Reduction or prevention in the cosmetic appearance or prevalence of the signs or symptoms of, e.g. aged, skin may mean that there is a reduction in the number and/or severity of the sign or symptom. For instance, the number of fine lines and wrinkles may be reduced and/or the size, e.g. the depth, i.e. the volume, of the wrinkles or fine lines may be reduced or minimized. Furthermore, reduction or prevention may involve stopping, or reducing the rate of, the appearance of new signs or symptoms.

"Dry skin" as referred to herein refers to an epidermis that lacks moisture or sebum, often characterized by a pattern of fine lines, scaling, and an itching and/or burning feeling. In some embodiments, dry skin refers to skin in which the *Stratum corneum* has a water content of less than about 10%, e.g. less than about 9, 8, 7, 6, or 5%.

In this respect, the reduction of dry skin, skin roughness (scaling), fine-lines or transepidermal water loss may be achieved by the moisturizing effects of the composition described above.

Thus, the invention may be seen to provide a cosmetic method of moisturizing skin of a mammalian animal, wherein a cosmetic composition as defined herein is administered to said animal. Alternatively viewed, the invention may be seen to provide a cosmetic method of increasing the water content of the *Stratum corneum* of a mammalian animal from less than about 10% to a range of about 10-30%, wherein a cosmetic composition as defined herein is administered to said animal.

Alternatively stated, the present invention provides a cosmetic composition as described herein for use in moisturizing skin of a mammalian animal, i.e. for using in increasing the water content of the *Stratum corneum* of a mammalian animal from less than about 10% to a range of about 10-30%. (The compound or composition may alternatively be used to prepare a cosmetic medicament for that purpose.)

"Moisturizing" as referred to herein covers moisturizers which prevent loss of water from the skin (e.g. TEWL) as well as moisturizers (humectants) that attract and retain water when applied to the skin and emollients (which improve defective desquamation).

As mentioned above, such moisturizing properties are advantageous for improving the cosmetic appearance of skin. In a particularly preferred embodiment, the skin is the skin of the face, ears, neck, hands or scalp, preferably the face, neck and/or ears.

"Wrinkles" are folds, ridges or creases in the skin. Skin wrinkles typically appear as a result of ageing processes. In this respect, the dermis comprises many of the structural elements of skin, which include collagen, which gives the skin its strength, glycosaminoglycans which give the skin its turgor, and elastin fibres which give the skin its elasticity or spring.

As the skin ages, the dermal layer gets thinner and the skin also produces less collagen. Moreover, the elastin fibres that provide elasticity wear out. These changes in the scaffolding of the skin cause the skin to wrinkle and sag. The rete-ridges of the dermal-epidermal junction flatten out, making the skin more fragile and making it easier for the skin to shear. This process also decreases the amount of nutrients available to the epidermis by decreasing the surface area in contact with the dermis, also interfering with the skin's normal repair process.

In the subcutaneous layer the fat cells get smaller with age. This leads to more noticeable wrinkles, sagging (laxity) and a loss of skin firmness and smoothness, as the fat cells cannot "fill in" the damage from the other layers.

Exposure to UVA and UVB radiation, i.e. sunlight, causes collagen to break down at a higher rate than with just chronologic ageing. Sunlight damages collagen fibres and causes the accumulation of abnormal elastin. It is thought that UV irradiation from sunlight results in oxidative stress from excessive generation of reactive oxygen species, which results in cell apoptosis and the breakdown of collagen. When sun-induced elastin accumulates, matrix metalloproteinases (MMP) are produced in large quantities. Normally, metalloproteinases remodel sun-injured skin by manufacturing and reforming collagen. However, this process does not always work well and some of the metalloproteinases actually break down collagen. This results in the formation of disorganized collagen fibres known as solar scars. The repetition of this imperfect rebuilding/regeneration process causes wrinkles to develop and skin laxity.

However, as mentioned above, the compositions described herein have been shown to reduce oxidative damage associated with exposure to UV radiation. It is thought that the polyphenolic compounds in the compositions of the invention may offer UV-scattering and UV-absorbing qualities in addition to the ability to scavenge free-radicals after exposure to UV. Thus, the compositions of the invention are advantageous in reducing or preventing the formation of wrinkles and skin laxity.

In a further preferred aspect, the compositions of the invention may also reduce the appearance of hyperpigmentation (e.g. dark spots) of the skin.

Hyperpigmentation may occur as a result of age or may result from premature ageing due to e.g. photo-aging. Altered pigmentation may result from a local excess of melanocytes or increases in melanocyte activity, or both. Pigmentation disorders include liver, sun or age spots (solar lentigo), melasma and other blemishes such as freckles.

As referred to herein "improving" the cosmetic appearance of skin is determined relative to normal optimum skin. Thus, in the case of photo-aged skin, normal optimum skin may be healthy, hydrated, normally pigmented skin of a subject of a similar age that has not experienced chronic exposure to sunlight. In the case of chronologically-aged skin, normal optimum skin may be healthy, hydrated, normally pigmented skin of a younger (adult) subject, e.g. at least 5 years younger, such as at least 10 years younger, than the subject to be treated. Hence, one or more of the signs or symptoms of ageing may be measured and compared to the same signs of skin that is normal optimum skin relative to the subject to be treated. Preferably an improvement is the reduction in one or more of the signs or symptoms of ageing.

As used herein, "treating" refers to the reduction, alleviation or elimination, preferably to normal levels, of one or more of the cosmetic symptoms or effects of said cosmetic condition or disorder e.g. presence or extent of dry skin, fine lines, wrinkles, skin roughness, extent or area of pigmentation, etc. relative to the symptoms or effects present on a different part of the body of said individual where the skin does not suffer from said condition or disorder and not subject to said treatment or in a corresponding "normal" individual not subject to said treatment, as described above.

"Preventing" or "reducing" refers to absolute prevention, or reduction or alleviation of the extent or timing (e.g. delaying) of the onset of that symptom or effect. For example conditions typified by dry, abnormally pigmented, wrinkled or rough skin may be prevented by regular application of compositions described herein before the appearance of such a condition.

Preferably said treatments are achieved using the compositions described herein.

The concentration of additional active ingredients in compositions of the invention, depends upon the mode of administration, the course of treatment, the age and weight of the subject, the cosmetic indication, the body or body area to be treated and may be varied or adjusted according to choice. Generally however, concentration ranges for the additional active ingredients described herein is 0.0001, 0.0005, 0.001 or 0.01 to 50%, e.g. 0.0005-40%, e.g. 0.01 to 25%, such as 0.1 or 0.5 to 5, e.g. 1-5% (w/w or v/v of the final preparation for administration, particularly for topical administration).

Effective single doses for the compositions of the invention may lie in the range of from about $1-20 \times 10^{-5}$ ml/cm$^2$/day, e.g. $2-15 \times 10^{-5}$ ml/cm$^2$/day, $3-10 \times 10^{-5}$ ml/cm$^2$/day, such as about $5 \times 10^{-5}$ ml/cm$^2$/day. Thus, in terms of the amount of chaga extract, i.e. active ingredient, an effective single does may lie in the range of from about $2 \times 10^{-4}$-$10 \times 10^{-3}$ mg/cm$^2$/day, e.g. $3 \times 10^{-4}$-$9 \times 10^{-3}$ mg/cm$^2$/day, $4 \times 10^{-4}$-$8 \times 10^{-3}$ mg/cm$^2$/day, $5 \times 10^{-4}$-$7 \times 10^{-3}$ mg/cm$^2$/day, $6 \times 10^{-4}$-$6 \times 10^{-3}$ mg/cm$^2$/day, $7 \times 10^{-4}$-$5 \times 10^{-3}$ mg/cm$^2$/day, $8 \times 10^{-4}$-$4 \times 10^{-3}$ mg/cm$^2$/day, $9 \times 10^{-4}$-$3 \times 10^{-3}$ mg/cm$^2$/day, such as about $1-2 \times 10^{-3}$ mg/cm$^2$/day when applied topically, depending on the mammalian animal being treated, taken as a single dose.

Animals (i.e. subjects) to which the compositions may be applied or administered are limited to mammals. Preferably the mammals are primates, domestic animals, livestock and laboratory animals. Thus preferred mammalian animals include mice, rats, rabbits, guinea pigs, cats, dogs, monkeys, pigs, cows, goats, sheep and horses. Especially preferably the compositions are applied, or administered, to humans.

The following Examples are given by way of illustration only in which the Figures referred to are as follows.

EXAMPLES

Example 1—Antioxidative Effect of Chaga Extracts

A cellular antioxidant activity (CAA) assay for quantifying the antioxidant activity of the chaga extract was performed according to Wolfe and Liu (J. Agric. Food Chem., 2007, 55 (22), pp 8896-8907). Dichlorofluorescin is a probe that may be trapped within cells and is easily oxidized to fluorescent dichlorofluorescein (DCF). The method measures the ability of compounds to prevent the formation of DCF by 2,2'-azobis(2-amidinopropane) dihydrochloride (ABAP)-generated peroxyl radicals in human hepatocarcinoma HepG2 cells. The decrease in cellular fluorescence when compared to the control cells indicates the antioxidant capacity of the test compounds. The antioxidant activities of various concentrations of chaga extract were evaluated using the CAA assay, and the results were expressed relative to the antioxidative capacity of quercetin and luteolin.

A chaga extract powder was prepared using a hot-water extraction method, as described herein. The chaga extract powder contained 25±5% (w/w) β-glucans and 5±1% (w/w) polyphenols. The chaga extract powder was dissolved in water to provide solutions with concentrations of 1 µg/ml, 0.5 µg/ml and 0.25 µg/ml, which were assessed using the assay described above.

Figure 1:
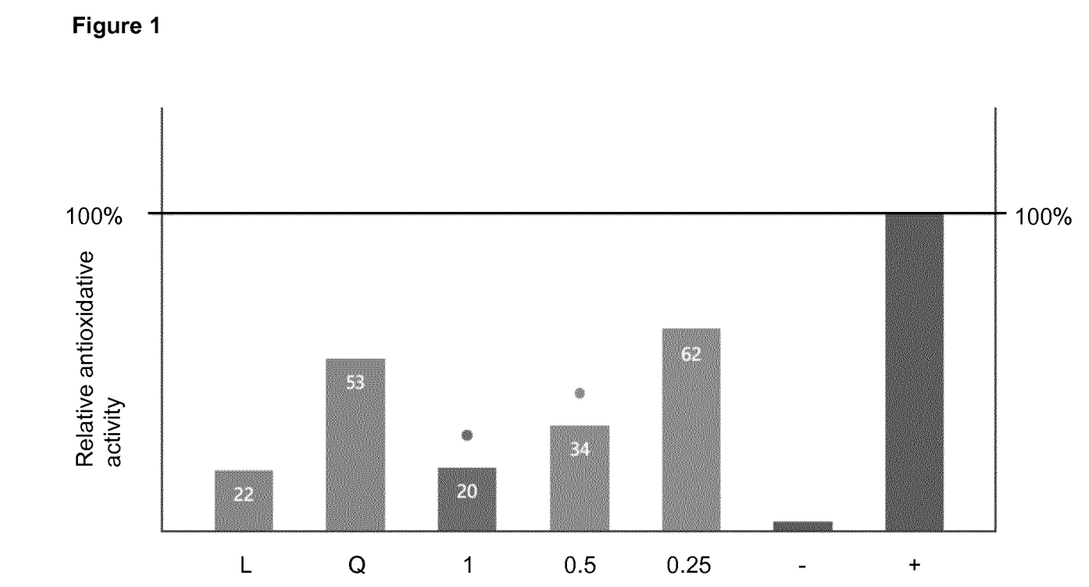
FIG. 1 shows a bar chart showing the antioxidative activity of chaga extract solutions relative to well-known antioxidants, luteolin and quercetin. L=luteolin; Q=quercetin; numbers=µg of chaga extract per ml in test solution; −=no dichlorofluorescin probe; and +=no test agent, i.e. full oxidation of dichlorofluorescin to Dichlorofluorescein.

FIG. 1 shows that all of the chaga extract solutions show antioxidative activity, wherein solutions containing a concentration of at least 0.5 µg/ml are particularly effective. Notably, the bar chart demonstrates that a chaga extract solution containing 1 µg/ml is able to reduce oxidative damage by 80% within 60 minutes.

Example 2—Effect of a Cosmetic Composition Comprising Chaga Extract on Skin Thickness and Wrinkle Formation after Exposure to UV-Radiation A 3-D in vitro skin model (Epistem Ltd) was used to assess the effect of a cosmetic composition containing chaga extract relative to retinol. In essence, the skin model is produced using freshly isolated human keratinocyte and fibroblast cells, which are subsequently cultured within a collagen gel at the air-liquid interface for up to 10 days. Test agents can be delivered topically and systemically via the culture media.

A cosmetic composition containing 5 mg/ml of the chaga extract powder described in Example 1 was prepared in a water base at a pH of 6.0-7.0. Various test agents, i.e. the chaga extract containing cosmetic composition or a composition comprising a high concentration of retinol, were applied topically to the in vitro skin model, which was exposed repeatedly to UV radiation. The skin thickening and formation of wrinkles was measured relative to in vitro skin samples that were not contacted with any compositions and had no exposure to UV radiation (negative) or full exposure to UV radiation (positive).

Figure 2:
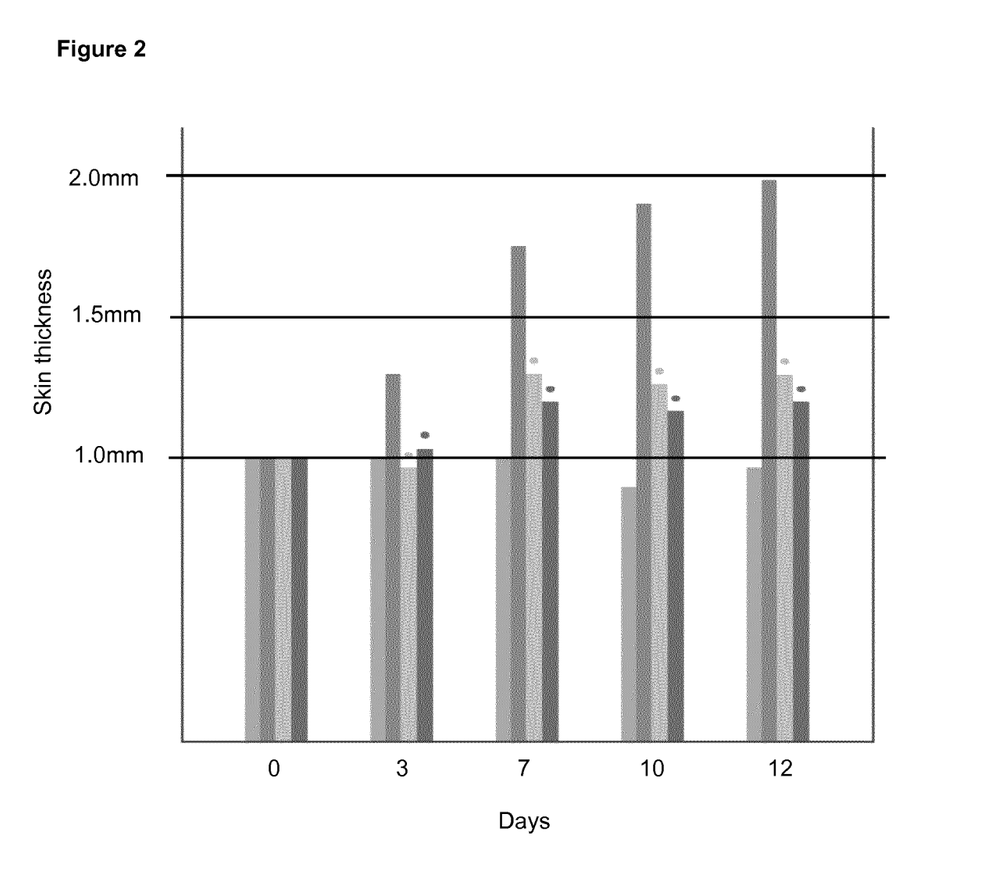
FIG. 2 shows a bar chart showing skin thickness (mm) over a number of days following treatment with test compounds and repeated exposure to UV radiation. The four columns, left to right, for each time point are: negative control (i.e. no exposure to UV or test compound); positive control (exposure to UV but no test compound); retinol (exposure to UV and treatment with high concentration retinol composition); and chaga extract (exposure to UV and treatment with composition comprising 5 mg/ml chaga extract).

FIG. 2 demonstrates that the cosmetic composition comprising 5 mg/ml of chaga extract was effective at reducing skin thickening and wrinkle formation caused by exposure to UV radiation. In fact, the composition comprising chaga extract was capable of almost completely suppressing UV-induced skin thickening and wrinkle formation. Notably, the composition comprising chaga extract was more effective than the composition containing a high concentration of retinol.

Example 3—Effect of a Cosmetic Composition Comprising Chaga Extract on Epidermal Volume and Smoothness The in vitro skin model described in Example 2 was used to assess the effect of the cosmetic composition of the invention on epidermal volume and smoothness.

A cosmetic composition containing 5 mg/ml of the chaga extract powder described in Example 1 was prepared in a water base at a pH of 6.0-7.0 and applied topically to the skin model.

Figure 3:
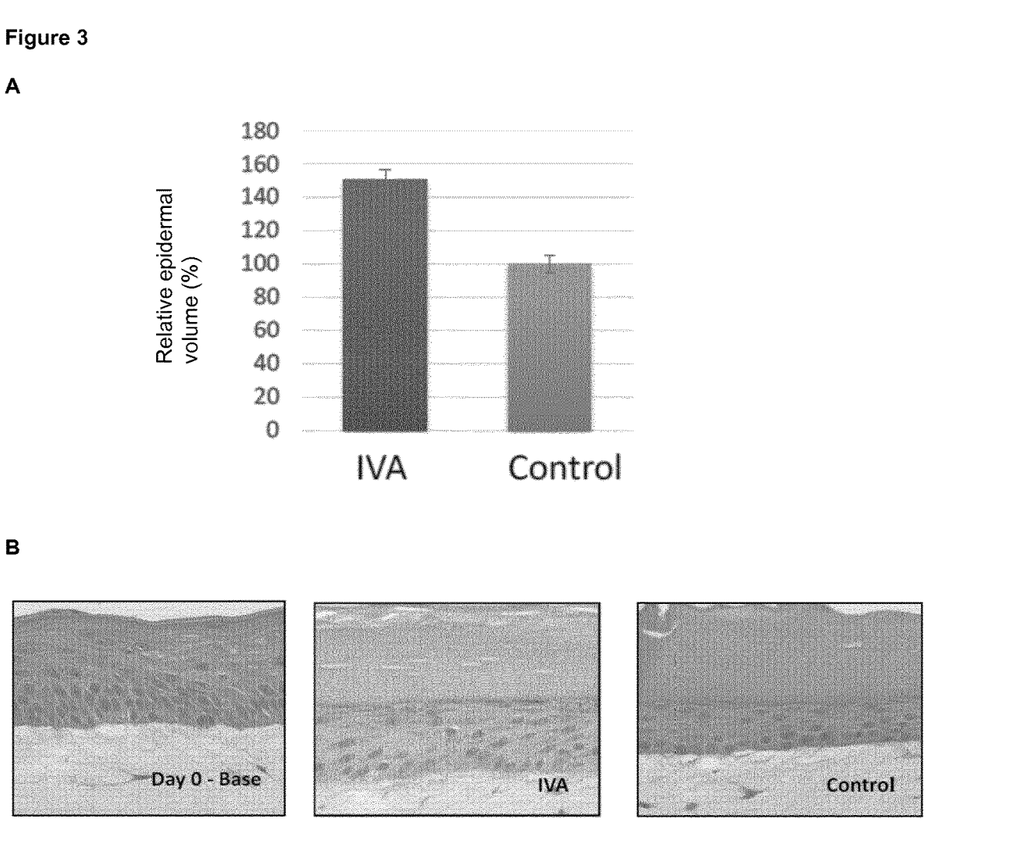
FIG. 3 shows (A) a bar chart showing the change in epidermal volume following treatment with a composition of the invention (IVA) relative to a control; and (B) photomicrographs of skin sections prior to treatment (Day 0—Base) and following treatment with a composition of the invention (IVA) and a control.

FIG. 3A demonstrates that the cosmetic composition of the invention resulted in a significant increase in epidermal volume (more than 50%) after one week relative to a control treatment. FIG. 3B shows that the skin surface also showed a significantly smoother appearance with even distribution of skin cells as a result from an improved epidermal performance.

Example 4—Self-Assessment Survey of Cosmetic Effects of a Composition Containing Chaga Extract A cosmetic composition containing 5 mg/ml of the chaga extract powder described in Example 1 was prepared in a water base at a pH of 6.0-7.0 and provided to 30 individuals with an age between 31-62 for testing. Subjects were asked not to use any skin care products 12 hours before initiating the test and were required to avoid extraordinary activities during the test period (e.g. extraordinary stress, extraordinary UV-exposure, invasive skin treatments). The treatment protocol is set out below:
1. Cleanse the skin;
2. Apply the composition to the face and let it be absorbed for two minutes;
3. Apply normal skin care products in addition to the composition;
4. Repeat steps 1-3 twice daily (morning and evening).

Figure 4:
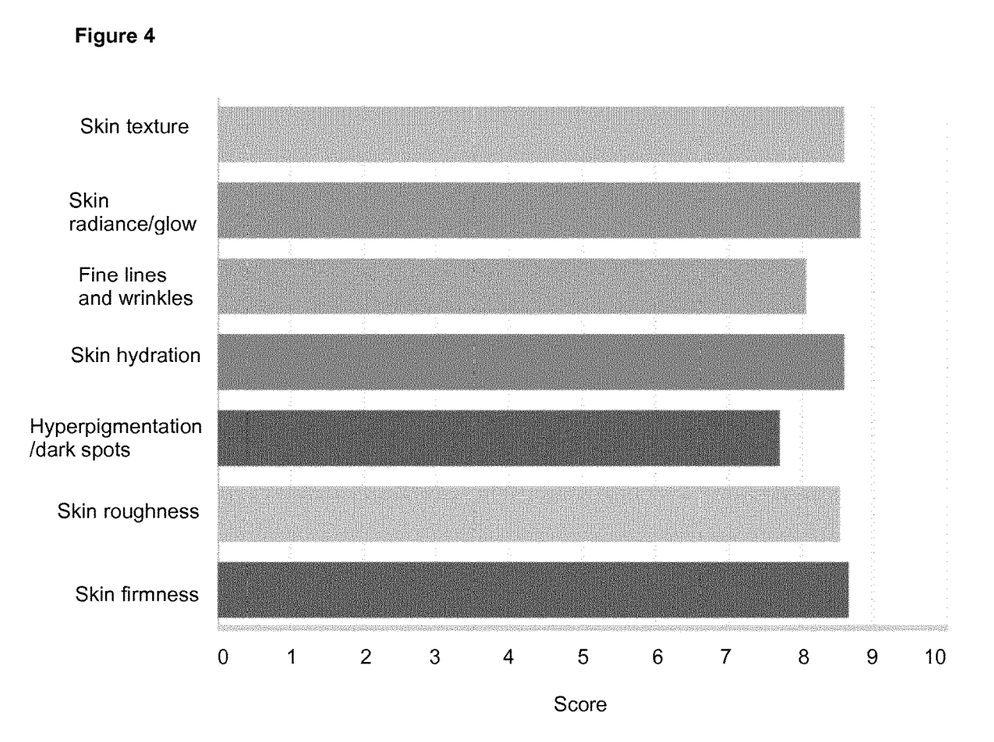
FIG. 4 shows a bar chart showing the results of a self-assessment survey of 30 subjects following a 10-day treatment protocol using a composition of the invention.

Subjects were requested to complete a questionnaire 10 days after initiating the protocol. The results of the self-assessment after only 10 days of use are shown in FIG. 4 and summarised below:
97% had improved skin texture
100% had improved radiance/glow
97% had reduced their fine lines and wrinkles
97% had improved skin hydration
87% had an improvement in hyperpigmentation/dark spots
93% had an improvement on skin roughness
97% had improved skin firmness All subjects completed the treatment protocol and self-assessment and no subjects showed any adverse effects.

The invention claimed is:

1. A cosmetic composition comprising:
   (i) a chaga extract at a concentration of at least about 2.5 mg/ml;
   (ii) vitamin C or a derivative thereof;
   (iii) vitamin E or a derivative thereof;
   (iv) vitamin B5 or a derivative thereof;
   (v) coenzyme Q10; and
   (vi) one or more physiologically or pharmaceutically acceptable excipients and/or diluents, wherein the chaga extract comprises at least about 1% (w/w) of β-glucans and at least about 0.10% (w/w) of polyphenolics and wherein the composition does not contain extracts of plants.

2. The cosmetic composition of claim 1, wherein the composition does not contain extracts of other fungi.

3. The cosmetic composition of claim 1, wherein the chaga extract is not a fermented chaga extract or extract thereof.

4. The cosmetic composition of claim 1, wherein the chaga extract has oxygen radical absorbance capacity (ORAC) of at least about 45000 μmol Trolox equivalents (TE) per 100 g.

5. The cosmetic composition of claim 1, wherein the chaga extract is obtained or obtainable by a method comprising the steps of:
   1) providing chaga mushroom dry matter;
   2) contacting water with the chaga mushroom dry matter of step 1) and incubating the resultant suspension for at least about 1 hour;
   3) removing solids from the suspension obtained from step 2) to obtain a chaga extract solution;
   4) optionally sterilizing the chaga extract solution from step 3); and
   5) producing a solid from the chaga extract solution of step 3) or 4).

6. The cosmetic composition of claim 5, wherein the water in step 2) is added to an approximate dry matter content of 1-20%.

7. The cosmetic composition of claim 5, wherein the step of incubating the suspension is performed at a temperature in excess of about 60° C.

8. The cosmetic composition of claim 5, wherein the extraction process in step 2) is performed under high pressure.

9. The cosmetic composition of claim 5, wherein the step of producing a solid from the chaga extract solution comprises spray-drying the solution.

10. The cosmetic composition of claim 1, wherein the vitamin C or a derivative thereof is sodium ascorbyl phosphate.

11. The cosmetic composition of claim 1, wherein the vitamin E or a derivative thereof is tocopherol acetate.

12. The cosmetic composition of claim 1, wherein the vitamin B5 or a derivative thereof is panthenol.

13. The cosmetic composition of claim 1, wherein said cosmetic composition is coated, impregnated or chemically bonded onto a product, material or device.

14. The cosmetic composition of claim 1, wherein said composition contains an effective amount of one or more agents to stabilize the chaga extract against degradation.

15. The cosmetic composition of claim 1, wherein said composition contains an effective amount of one or more preservatives or anti-microbials to prevent the spoilage of the composition.

16. The cosmetic composition of claim 14, wherein said one or more agents to stabilize the chaga extract against degradation is selected from EDTA, citrate, polysorbate, benzyl alcohol, urea or a combination thereof.

17. The cosmetic composition of claim 15, wherein said one or more preservatives or anti-microbials to prevent the spoilage of the composition is selected from EDTA, citrate, polysorbate, benzyl alcohol, urea or a combination thereof.

18. The cosmetic composition of claim 1, wherein said cosmetic composition comprises a skin-conditioning agent.

19. The cosmetic composition of claim 18, wherein the skin-conditioning agent is selected from humectants, exfoliants, emollients or mixtures thereof.

20. The cosmetic composition of claim 19, wherein the humectant is propylene glycol.

21. A method for improving the cosmetic appearance of skin of a mammalian animal comprising topically administering a cosmetic composition as defined in claim 1 to said animal.

22. The method of claim 21, wherein said skin is chronologically-aged skin.

23. The method of claim 21, wherein said skin is photo-aged skin.

24. The method of claim 21, wherein improving the cosmetic appearance of skin comprises reducing or preventing the appearance or prevalence of wrinkles, fine lines, hyperpigmentation, laxity, skin roughness, dry skin, and/or transepidermal water loss.

25. The method of claim 21, wherein improving the cosmetic appearance of skin comprises increasing skin hydration, firmness, smoothness and/or radiance.

26. The method of claim 21, wherein the skin of said animal is moisturized.

* * * * *